United States Patent [19]

Wong

[11] Patent Number: 4,694,173

[45] Date of Patent: Sep. 15, 1987

[54] NONDISPERSIVE GAS ANALYZER HAVING NO MOVING PARTS

[75] Inventor: Jacob Y. Wong, Santa Barbara, Calif.

[73] Assignee: Hibshman Corporation, San Luis Obispo, Calif.

[21] Appl. No.: 785,725

[22] Filed: Oct. 9, 1985

[51] Int. Cl.[4] .................. G01N 21/03; G02F 1/29
[52] U.S. Cl. ............................ 250/343; 250/339; 250/353; 356/437
[58] Field of Search .............. 250/339, 340, 341, 343, 250/353, 347, 345; 356/439, 438, 437, 436, 435, 434, 433

[56] References Cited

U.S. PATENT DOCUMENTS

| | | | |
|---|---|---|---|
| 2,824,235 | 2/1958 | Hahn, Jr. et al. | 250/351 |
| 3,383,460 | 5/1968 | Pritchard | 358/61 |
| 3,811,776 | 5/1974 | Blau, Jr. | 356/51 |
| 4,283,113 | 8/1981 | Eden | 350/96.15 |
| 4,515,472 | 5/1985 | Welch | 356/5 |
| 4,549,080 | 10/1985 | Baskins et al. | 250/343 |

Primary Examiner—Janice A. Howell
Assistant Examiner—Constantine Hannaher
Attorney, Agent, or Firm—Daniel C. McKown

[57] ABSTRACT

A multi-component non-dispersive gas analyzer of a type typically used to measure the concentrations of gases present in automotive emissions and in breath analyzers has no moving parts and employs electrically operated means for effectively inserting and removing a reference cell from the optical path and for selecting a particular filter to determine momentarily the wavelengths of radiation being examined. The means for accomplishing these ends include a substrate on which a layer of vanadium dioxide is deposited. The layer is a good reflector at temperatures greater than 67° C. and reflects only slightly at lower temperatures. The layer is alternately heated by an electrical current and is then allowed to cool to provide the desired optical switching action. This electrically-controlled selectively reflective layer is then used in conjunction with the reference cell and with an array of filters to implement the necessary switching and selection of the components.

35 Claims, 15 Drawing Figures

NONDISPERSIVE GAS ANALYZER HAVING NO MOVING PARTS

BACKGROUND OF THE INVENTION

1. Field of the Invention

The present invention is in the field of non-dispersive gas analyzers of a type typically used to measure the concentrations of specified gases in automotive emissions and in breath analyzers. More specifically, the present invention relates to apparatus having no moving parts and capable of measuring the concentrations of one or more specified components in a mixture of gases.

2. The Prior Art

The term "nondispersive" as used herein refers to the apparatus used, typically a narrow-band optical or infrared filter instead of a prism or diffraction grating, for isolating for purposes of measurement the radiation in a particular wavelength band that normally coincides with a strong absorption band in the absorption spectrum of a gas to be measured.

As discussed in U.S. Pat. No. 3,811,776 to Blau, Jr., nondispersive gas analyzers typically incorporate, in addition to the narrow band filter, a gas cell containing the gas of interest, and an identical cell evacuated or filled with a gas that is transparent at the wavelength used. Typically, these cells alternately are moved into and out of a radiation beam. In another common arrangement, two beams are used and apparatus is provided for switching between the alternative beams.

Typically, both the alternative movement of the cells or switching of the beams is accomplished by rotating machinery. The use of such rotating machinery has generally been considered necessary but undesirable. Typical problems included noise, vibration, size and weight, electrical noise from the driving motor, and wear of the bearings.

Typically, these problems are compounded where the analyzer is required to measure several components.

The present inventor recognized that the problems associated with the rotating machinery of prior art gas analyzers could be overcome by employing solid-state devices to accomplish the desired switching action, thereby making possible a gas analyzer having no moving parts.

It has long been known that certain materials such as germanium, silicon, cadmium sulphide, zinc oxide, and certain glasses are characterized in that their optical transparency characteristics in terms of wavelength of light vary with the temperature of the material, as discussed in U.S. Pat. No. 2,824,235 to Hahn, Jr., et al.

In U.S. Pat. No. 4,283,113, Eden discloses the use of a thin film of a vanadium oxide, switchable between a high-reflectance state and a high-transmission state for switching a light signal between optical fibers. The thin film is alternately heated and cooled by thermoelectric junctions placed in thermal contact with the edges of the substrate on which the thin film is deposited.

In U.S. Pat. No. 4,515,472, Welch discloses the use of a scanning electron beam to produce localized heating in a vanadium dioxide layer. The localized heating produces a highly reflective small spot on the otherwise transmissive vanadium dioxide layer.

Thus, although the characteristics of vanadium dioxide and certain other thin films were known in the art, it remained for the present inventor to show that such films could advantageously be combined with certain other optical components to produce uniquely useful combinations that make possible a multicomponent gas analyzer having no moving parts.

SUMMARY OF THE INVENTION

It is an object of the present invention to provide non-moving apparatus for effectively inserting and removing a gas cell from a beam of radiation.

In accordance with a preferred embodiment, the present inventor positions a layer of a material, such as vanadium dioxide, that has selectably a highly-reflective state and a slightly-reflective state behind the gas cell, so that a fraction of the incoming beam of radiation is reflected from the front window of the cell to a detector, while another fraction of the incoming radiation passes through the cell to impinge on the selectively reflective material, from which, depending on the state of the material, it may or may not be reflected from the material back through the gas cell to the detector.

In an alternative embodiment, the present inventor positions a layer of a material that has selectably a highly-reflective state and a highly-transmissive state ahead of the gas cell so that when the material is in its highly reflective state the incoming radiation is predominantly reflected from the material to a detector, and when the material is in its highly-transmissive state, the incoming radiation is passed through the material and into the gas cell. A reflective surface in the gas cell reflects the radiation back out through the front window of the gas cell to the detector.

Several other variations and embodiments will be discussed below.

Another object of the present invention is to provide an article having no moving parts for applying polychromatic radiation to a selected one of N filters so that the filtered radiation can then be measured.

In a preferred embodiment, this is accomplished by providing a first opaque plate that intercepts the entire beam of polychromatic radiation and that has N apertures, each of which is covered by a different one of N filters. Some of the intercepted beam passes through each of the filters and impinges on one of N independently-operable selective reflectors, each of which has selectably a highly-reflective state and a slightly-reflective state. Normally, only one of the independently-operable selective reflectors will be set to the highly-reflective state, and the remaining reflectors will be maintained in the slightly-reflective state. The radiation impinging on the highly-reflective reflector will then be redirected back through the corresponding filter for further optical or photoelectric processing.

In an alternative embodiment, the polychromatic radiation impinges on a first opaque plate that has N apertures, each of which is covered by one of N filters. After passing through those filters, components of the radiation beam impinge on independently-operable radiation gates, each of which has, selectably, a transmissive state and a non-transmissive state. Normally, only one of the radiation gates is in the transmissive state, and by selecting which radiation gate is in the transmissive state, the choice of filter is effected. In a variation on this embodiment, the radiation gates are encountered first by the beam of polychromatic radiation, and only that part of the beam that is passed by a gate reaches a particular one of the N filters. Thus, in this variation, the relative position along the beam of the filters and of the radiation gates are reversed from the positions described in connection with the alternative embodiment.

It is a further objective of the present invention to provide a multi-component analyzer having no moving parts. In accordance with a preferrred embodiment of the invention, after a beam of light has been passed through a sample, the beam is intercepted by apparatus having no moving parts and which selectively passes a fraction of the beam through a selected one of a number of filters to produce a filtered beam. Thereafter, the filtered beam is applied to a second apparatus, also having no moving parts, that in response to an applied electrical signal alternately either applies the filtered beam directly to a detector or first passes the filtered beam through a reference cell and then to the detector.

In an alternative embodiment of the multi-component analyzer of the present invention, the beam is first passed through a sample to be analyzed, which results in a characterized beam. The characterized beam is then intercepted by a first apparatus having no moving parts and responsive to an electrical signal for producing an output beam that consists alternately of either the characterized beam or a beam obtained by passing the characterized beam through a reference cell. In either case, the output beam is applied to a second apparatus that has no moving parts and that includes more than one filter. The second apparatus is responsive to an applied electrical signal for selectively passing the beam through a selected one of several filters to produce a filtered beam, which is then applied to a detector.

These and other objectives and advantages of the present invention will become clear from the detailed description given below in which several preferred embodiments are described in relation to the drawings. The detailed description is presented to illustrate the present invention, but is not intended to limit it.

DETAILED DESCRIPTION OF THE PREFERRED EMBODIMENT

Analyzers of the type under discussion are used to measure the concentration of a component that may be present in a gaseous or liquid sample. The concentration of the component to be measured is determined by the amount of absorption that occurs when a beam of radiation is passed through the sample. Normally, the wavelength of the radiation would be selected to coincide with a relatively strong absorption band that is characteristic of the component to be measured. The wavelength actually used is typically in the infrared portion of the spectrum, but in theory, the visible and ultraviolet portions of the spectrum could also be used. As used herein, the word beam denotes directed radiation, and as used herein, the beam may be collimated, converging, or diverging.

Several techniques, each having its own variations may be used to measure the concentration of a component. In the simplest technique, a hollow cell is used, and the intensity of the radiation transmitted through the cell is measured with the cell empty, and is then measured again with the cell filled with a sample that includes the component. The reduction in the transmitted radiation observed when the cell is filled can then be related to the concentration in the sample of the component being measured. Inherent in this technique is the need to alternately include the sample in the beam of radiation and then to exclude the sample from the beam of radiation. As will be seen from the discussion below, this can be accomplished expeditiously by using the apparatus of the present invention.

Figure 1:
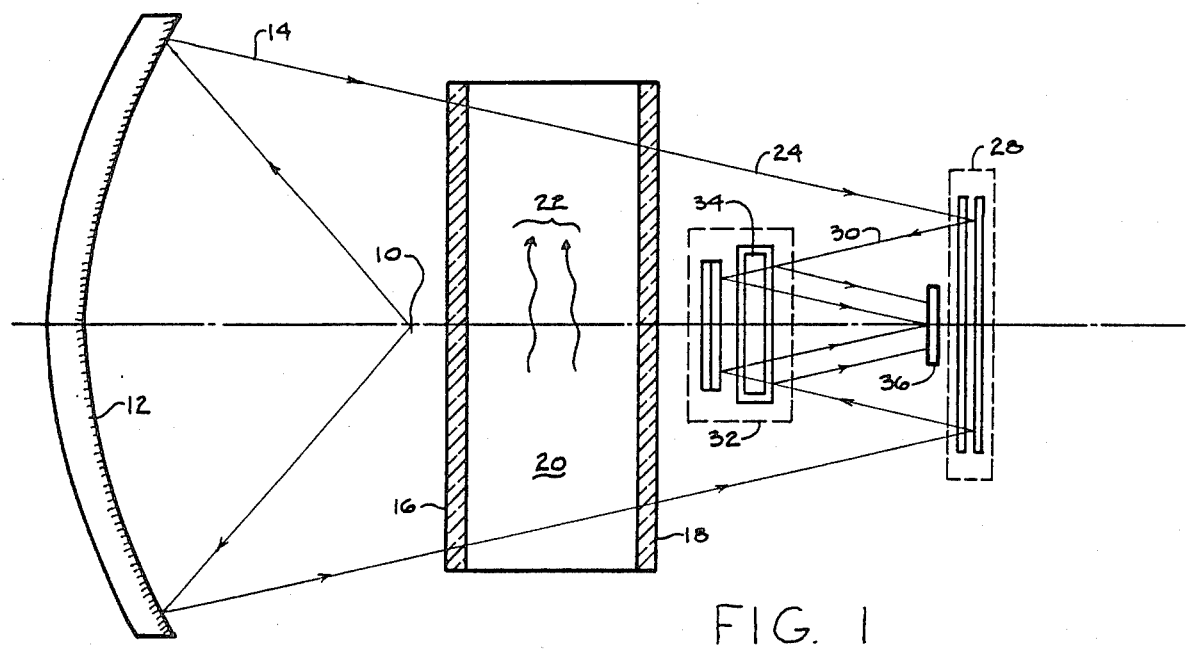
FIG. 1 is an optical diagram showing the optical system in a preferred embodiment of the multi-component gas analyzer of the present invention.
Figure 2:
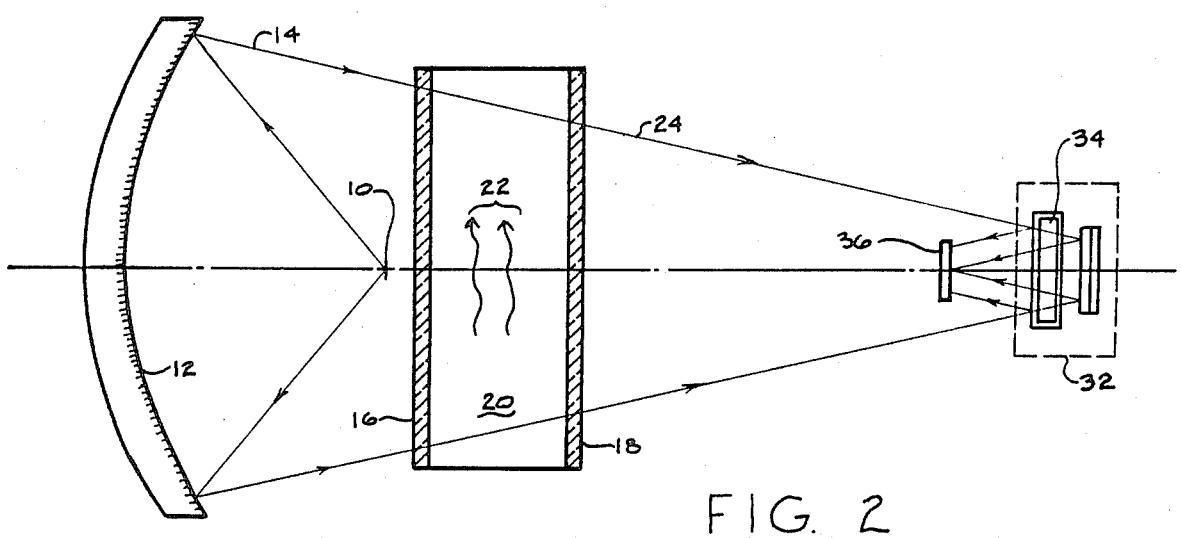
FIG. 2 is an optical diagram showing the optical system in a single-component gas analyzer in accordance with the present invention.

A second, more sophisticated and more accurate technique is known in the industry as the "negative filtering" method. In that method, the sample always remains in the optical path, while a reference amount of the component (included in a reference cell) is alternately inserted into and removed from the optical path. Thus, in the negative filtering technique, a known incremental amount of the component causes an incremental amount of absorption. This permits the derivative of absorption with respect to concentration to be determined, and this derivative is a function of the concentration. Therefore, the concentration can be found from the value of the derivative. The negative filtering technique is the preferred technique for use in the present invention and is illustrated in FIGS. 1 and 2. However, it should now be clear that the apparatus and method of the present invention are not limited to the negative filtering technique.

FIG. 1 shows the optical system in a preferred embodiment of a multi-component analyzer in accordance with the present invention. In the configuration shown, the negative filtering technique is used. FIG. 2 shows the optical system for use in a single-component analyzer in accordance with the present invention.

A continuously-emitting polychromatic source 10 of radiation is used in the preferred embodiment. Radiation emitted by the source 10 is collected by the mirror 12 and formed into a converging beam 14. In alternative embodiments, a lens may be used instead of the mirror 12 to produce the beam 14. The beam 14 is passed through the sample space or airway 20 defined by the windows 16, 18. The sample to be analyzed is located in the space 20, and in the embodiment shown, the sample is a flow of gas as indicated by the arrows 22. From the window 18 emerges the characterized beam 24, the spectral characteristics of which have been modified by passage through the space 20 and which, accordingly, indicate the concentrations of various compoenents present in the sample in the space 20. In one variation of the preferred embodiment the characterized beam 24 is folded back on itself by a mirror.

In the multi-component analyzer of FIG. 1, the beam 24 is applied to the apparatus 28 which is an electrically-selectable filter. The filter 28 may be constructed in any of a number of ways which will be discussed below; a preferred embodiment of the apparatus 28 will be described in due course below in reference to the diagram of FIG. 4. The apparatus 28 permits selection of one or more filters, so that radiation of only certain selected wavelengths is present in the filtered beam 30.

The filtered beam 30 is then applied to an apparatus 32 that alternately, under control of an applied electrical signal, in effect inserts and removes the reference cell 34 from the beam. The apparatus 32 can have a number of forms as will be discussed below, and a preferred embodiment of the apparatus 32 will be described in due course below in reference to the diagram of FIG. 7. Both the radiation that has passed through the reference cell 34 as well as the radiation that does not pass through it are focused onto the detector 36, which produces an electrical signal related to the intensity of the applied radiation.

In the best known mode for operating the apparatus of FIG. 1, a first filter is selected by application of an electrical signal to the apparatus 28, and the wavelength interval passed by this filter corresponds to an absorption band of the first component to be analyzed. With the first filter in use, the intensity of the radiation reaching the detector 36 is measured with the reference cell 34 effectively, in the optical path and again with the reference cell 34 effectively removed from the optical path in response to electrical signals applied to the apparatus 32. Thereafter, a second electrical signal applied to the apparatus 28 results in selection of a second filter, and again the radiation reaching the detector 36 is measured with the reference cell 34 inserted into and removed from the optical path. This process is repeated for each of the components to be analyzed, and that constitutes one measure cycle. Because the selections can be made rapidly, a typical measurement cycle can be carried out in less than one second.

The apparatus of FIG. 2 is similar to that of FIG. 1, with the exception that it is limited to measuring the concentration of a single component present in the sample. The beam 24 is applied directly to the apparatus 32 which alternately effectively inserts and removes the reference cell 34 from the optical path.

For use in certain applications, for example where a high speed of response is required, it is possible to employ a number of systems similar to that shown in FIG. 2, one for each component.

In practicing the invention, it has been found possible to mount the apparatus 32 along with the detector 36 and the filter selecting apparatus 28 in a single TO-8 package. In a typical embodiment, the diameter of the mirror 12 is on the order of 2.5 centimeters.

In the embodiments of FIGS. 1 and 2, the reference cell must contain a known amount of the component being measured. So long as the gases in the reference cell do not interact chemically and so long as their absorption bands do not overlap, it is possible to include known amounts of the various components within the same reference cell 34.

Figure 3:
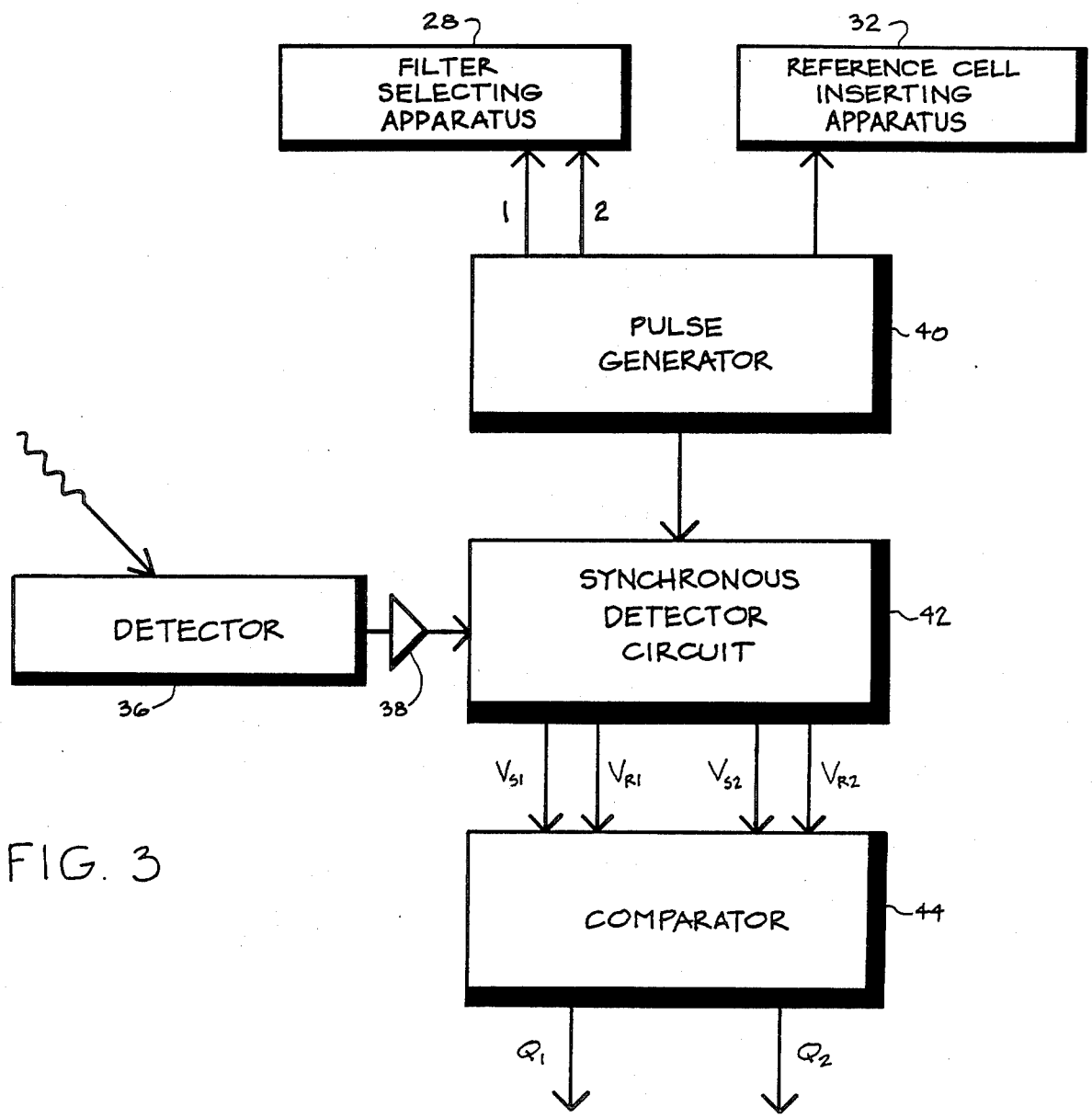
FIG. 3 is an electronic block diagram showing the electronic system used in the preferred embodiment of FIG. 1.

The operation of the multi-component analyzer of FIG. 1 is programmed by the electronic system shown in block diagram form in FIG. 3. A pulse generator 40 which includes a clock generates a cyclical sequence of pulses that are applied to the filter selecting apparatus 28 and to the reference cell inserting apparatus 32. The pulse generator 40 also applies pulses to the synchronous detector circuit 42 that permits identification of the electrical signal generated by the detector 36. That signal is passed through a preamplifier 38 to the synchronous detector circuit which functions like a multiplexer to apply the incoming electrical signal from the detector to one of the output lines $V_{S1}$, $V_{R1}$, $V_{S2}$, and $V_{R2}$. Here $V_{S1}$ is a signal representing the detector output when the reference cell is effectively out of the optical path when the first component is being measured, $V_{R1}$ is a signal representing the detector output when the reference cell is effectively in the optical path and the first component is being measured, $V_{S2}$ is a signal representing the detector output when the reference cell is effectively out of the optical path and the second component is being measured, and $V_{R2}$ is a signal representing the detector output when the reference cell is effectively in the optical path and the second component is being measured. These signals are applied to the comparator circuit 44 which compares $V_{S1}$ and $V_{R1}$ to obtain a quantity $Q_1$ that can be calibrated to the concentration of the first component in the sample. The comparator 44 also compares the signals $V_{S2}$ and $V_{R2}$ to obtain the signal $Q_2$ that can be calibrated to the concentration of the second component in the sample. The extension of this technique to the case where more than two comoonents are present is apparent.

In the preferred embodiment, the comparator 44 calculates $Q_1$ and $Q_2$ from the signals $V_{S1}$, $V_{R1}$, $V_{S2}$, and $V_{R2}$ as follows:

$$Q_1 = \frac{V_{S1}}{V_{R1} - V_{S1}} \text{ and } Q_1 = \frac{V_{S2}}{V_{R2} - V_{S2}}$$

Techniques for relating $Q_1$ and $Q_2$ to the concentrations of the first and second component, respectively, are well-known in the art.

Figure 4:
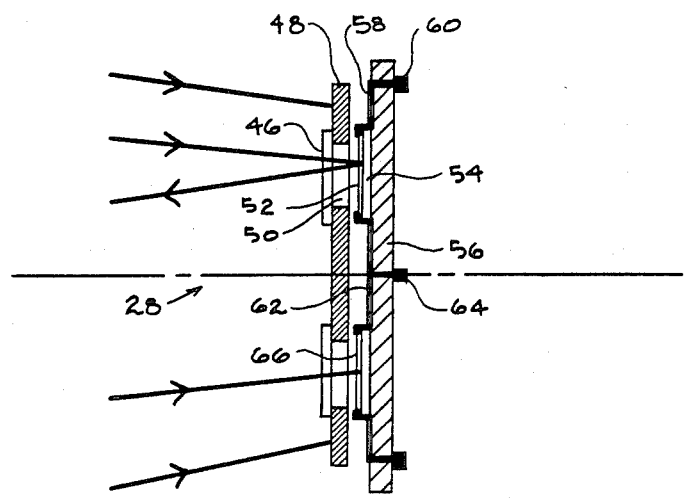
FIG. 4 is a diagram showing in cross section an electrically selectable filter of the type used in the preferred embodiment of FIG. 1.

FIG. 4 shows in cross section an electrically selectable filter of the type used in the preferred embodiment of FIG. 1.

In the preferred embodiment, the electrically-selectable filter 28 includes a first opaque plate 48 having a number of apertures of which the aperture 50 is typical. A different filter, of which the filter 46 is typical covers each of the apertures. Accordingly, radiation of a different selected wavelength passes through each of the apertures.

A second plate 56 is positioned parallel to the first plate 48, and in the preferred embodiment, the plate 56 is composed of an electrically insulative material. Substrates 54 are located on the second plate 56 directly behind (opposite) the apertures in the first opaque 48. The face of the substrate 54 which faces the aperture 50 is coated with a thin film of vanadium dioxide 52, which is selectively reflective depending on its temperature. The temperature of the layer 52 is altered by electrically heating the substrate 54. This is accomplished in the preferred embodiment by providing conductive leads 58, 62 that terminate in the terminals 60, 64 respectively. The terminal 64 is common to all of the substrates.

When no current is flowing through the conductors 58, 62, the layer 52 is in its semiconductive slightly-reflective state, but when the current is applied, the temperature of the substrate 54 increases, and when the temperature reaches 67° C. the layer 52 changes state to its conductive and highly-reflective state. As shown in FIG. 4, the layer 52 is in its reflective state, and therefore reflects the incoming radiation back out through the filter 46, while the layer 66 is in its slightly-reflective state and does not appreciably reflect the incoming radiation. The various apertures 50 are spaced around a circle in the preferred embodiment.

Figure 5:
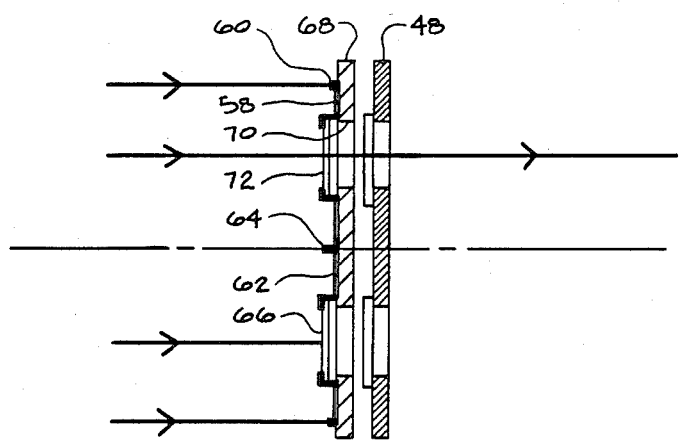
FIG. 5 is a diagram showing in cross section a first alternative embodiment of an electrically selectable filter.
Figure 6:
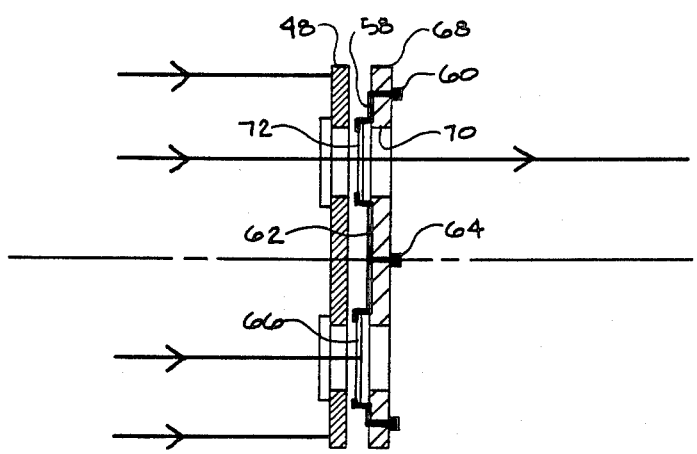
FIG. 6 is a diagram showing in cross section a second alternative embodiment of an electrically selectable filter.

FIGS. 5 and 6 are alternative embodiments of an electrically selectable filter. Those embodiments employ independently-operable radiation gates for selectively transmitting or not transmitting an incoming beam of radiation. This is accomplished by applying a film of vanadium dioxide to a substrate that is substantially transparent to radiation of the wavelength used. In one embodiment, the substrate is composed of a conducting glass and ohmic heating is employed. In another embodiment, the substrate is heated by conduction, while in other embodiments the substrate is heated by infrared or microwave radiation from an external source.

In FIGS. 5 and 6, the filter substrate 48 is substantially the same as was described in connection with the apparatus of FIG. 4.

The plate 68 of FIGS. 5 and 6 differs from the plate 56 of FIG. 4 in that it includes apertures of which the aperture 70 is typical, to permit passage of the radiation transmitted by the radiation gates of which the gate 72 is typical. Because the plate 68 is electrically insulative, the conductors 58, 62 and the terminals 60, 64 may be positioned on the plate in any convenient manner.

In FIGS. 5 and 6, the radiation gate 72 is in its transmissive state, while the radiation gate 66 is in its non-transmissive state.

Figure 7:
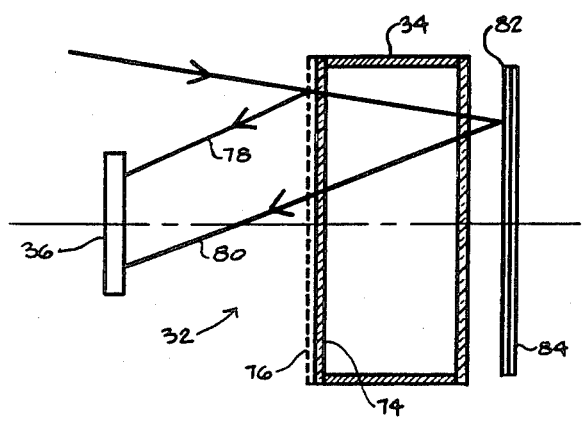
FIG. 7 is a diagram showing in cross section an electrically operated apparatus of the type used in the preferred embodiment of FIG. 1 for selectively inserting and removing a reference cell from a beam of radiation.

FIG. 7 is an optical diagram showing in cross section an electrically operated apparatus 32 of the type used in the preferred embodiment of FIG. 1 for selectively inserting and removing a reference cell 34 from a beam of radiation. A typical reference cell is hermetically sealed and contains one or more gases under specific partial pressures. The cell includes at least one window 74 through which radiation can enter the cell. Because its index of refraction is greater than that of the medium, there will be some reflection from the front face of the window 74; however, if this reflection is not adequate, an optional partially reflecting coating 76 may be added, as indicated by the dashed lines in FIGS. 7–10.

A fraction, represented by the ray 78, of the incoming radiation is reflected from the front surface of the cell, while another fraction represented by the ray 80 passes twice through the cell. It is this latter fraction that is alternately present and absent according to the state of the layer 82.

The layer 82 is composed of vanaium dioxide in a preferred embodiment, which is applied to a substrate 84. In a preferred embodiment, the substrate 84 is resistive, and is heated by passing an electric current through it.

When the current is applied, the layer 82 is heated to its metallic state in which it is highly reflective, and thereby the beam represented by the ray 80 is present. Alternately, the electrical current applied to the substrate 84 is interrupted, and the layer 82 then cools and assumes its semiconductive slightly-reflective state, so that the radiation represented by the ray 80 is enormously reduced. Both the radiation represented by the ray 78 and the radiation represented by the ray 80 are brought to bear on the detector 36 which sees an alternating component superimposed on a steady component.

As seen in FIG. 7, the ray 78 does not travel as far to reach the detector 36 as does the ray 80. Accordingly, the radiation reflected from the front of the window 34 does not come to a focus at the same axial location as the radiation reflected from the layer 82. Accordingly, the spot of radiation formed on the detector 36 may be larger than is desired. If this is the case, the problem can be remedied by imparting a slight curve to the substrate 84 as shown in FIGS. 8 and 10.

Figure 8:
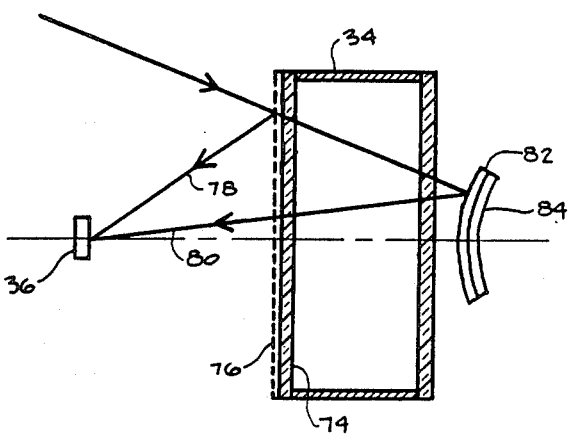
FIG. 8 is a diagram showing in cross section a variation of the electrically operated apparatus shown in FIG. 7.
Figure 9:
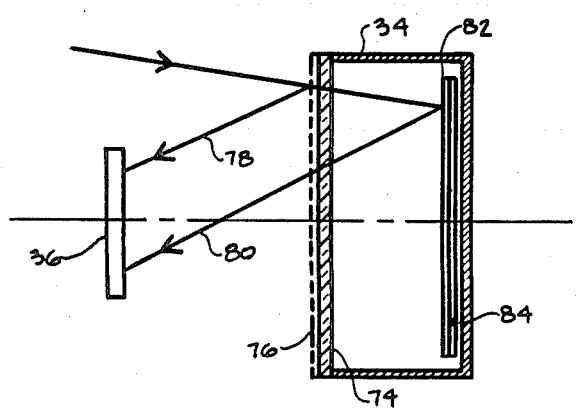
FIG. 9 is a diagram showing in cross section a second alternative embodiment of an electrically operated apparatus for selectively inserting and removing a reference cell from a beam of radiation.
Figure 10:
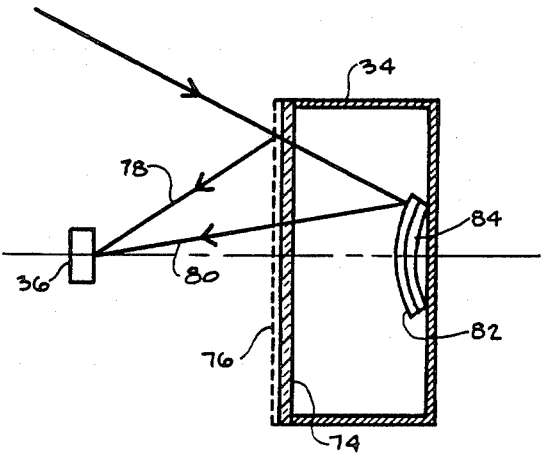
FIG. 10 is a diagram showing in cross section a variation of the electrically operated apparatus of FIG. 9.

FIGS. 9 and 10 differ from FIGS. 7 and 8, respectively, in that in FIG. 9 and 10 the substrate 84 and the layer 82 are located inside the cell 34.

The apparatus shown in FIGS. 7–10 makes use of a layer 82 that is selectably either highly reflective or only slightly reflective. In contrast, the embodiments shown in FIGS. 11–13 employ a layer that is selectably either highly reflective or highly tramsmissive. Accordingly, the layer 86 of FIGS. 11–13 must be applied to a substrate 88 that is transparent to the wavelength(s) that are used. In one embodiment, the substrate 88 is composed of a conductive transparent material such as tin oxide.

Figure 11:
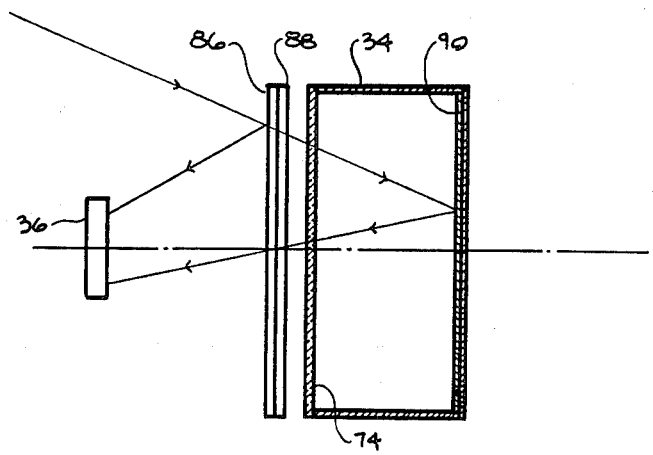
FIG. 11 is a diagram showing in cross section a third alternative embodiment of an electrically operated apparatus for selectively inserting and removing a reference cell from a beam of radiation.
Figure 12:
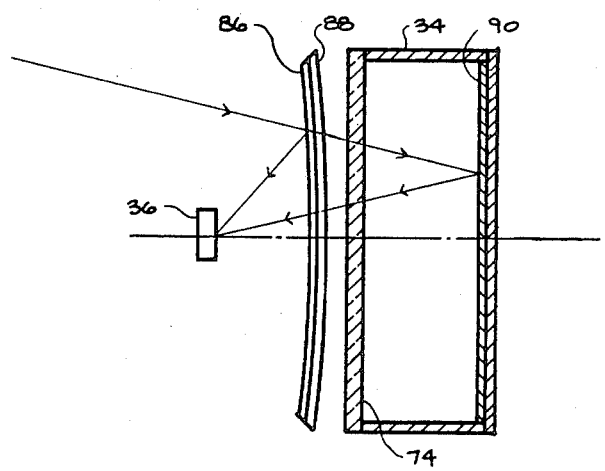
FIG. 12 is a diagram showing in cross section a first variation of the electrically operated apparatus of FIG. 11.

The embodiments of FIGS. 11 and 12 require that the cell 34 have a front window 74, but instead of an opposite exit window, a mirror 90 is used.

The embodiment of FIG. 12 differs from that of FIG. 11 in that the substrate 88 is curved in FIG. 12. Alternatively, the mirror 90 is curved in another embodiment.

Figure 13:
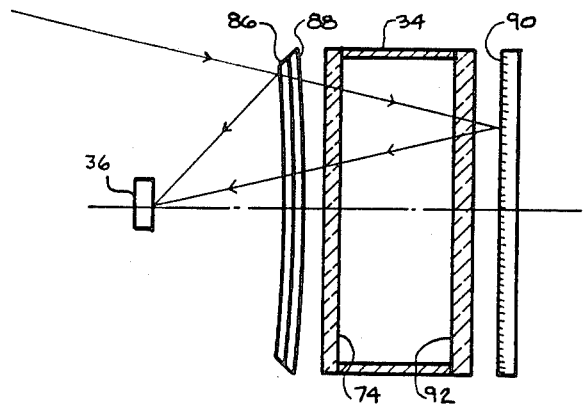
FIG. 13 is a diagram showing in cross section a second variation of the electrically operated apparatus of FIG. 11.

In the embodiment of FIG. 13, the cell 34 includes a second window 92, and the mirror 90 is located outside of the cell.

Figure 14:
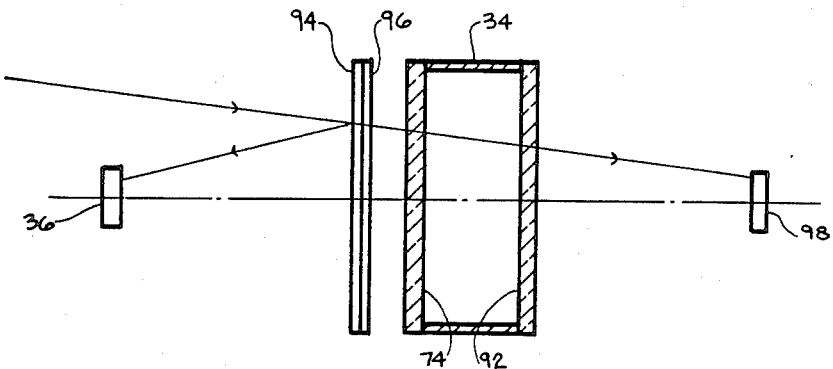
FIG. 14 is a diagram showing in cross section a fourth alternative embodiment of an electrically operated apparatus for selectively inserting and removing a reference cell from a beam of radiation; and, FIG. 15 is a diagram showing in cross section a fifth alternative embodiment of an electrically operated apparatus for selectively inserting and removing a reference cell from a beam of radiation.

The embodiment of FIG. 14 makes use of a layer 94 that is alternately reflective and transmissive. The reflective rays are collected at a first detector 36, while the transmitted rays pass through the cell 34 and are collected on the second detector 98.

Figure 15:
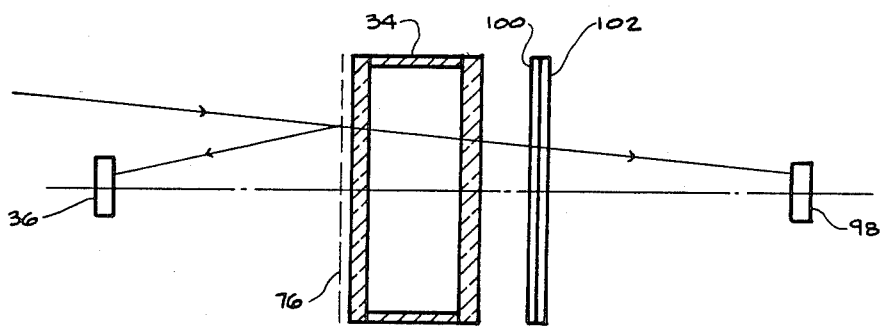

In the embodiment of FIG. 15, the layer 100 is alternately highly transmissive and slightly transmissive. It is mounted on the substrate 102 which, like the substrate 96 of FIG. 14 must be transparent. If necessary, an optional partially reflecting coating 76 can be applied to the front window of the cell 34.

Part of the radiation falling on the front of the cell 34 is reflected to the detector 36, while the remainder passes through the cell 34 and is alternately passed or not passed by the layer 100 to the detector 98.

Because it is very difficult in practice to obtain two detectors 36, 98 that have substantially the same characteristics, the embodiments of FIGS. 14 and 15 are considered to be less attractive than the other embodiments discussed above.

Thus, there has been described a preferred embodiment of a multi-component analyzer having no moving parts. It is seen that the features that make possible this significant achievement are the use of electrical shutters in combination with filters and reference cells.

The foregoing detailed description is illustrative of several embodiments of the invention, and it is to be understood that additional embodiments thereof will be obvious to those skilled in the art. The embodiments described herein together with those additional embodiments are considered to be within the scope of the invention.

What is claimed is:

1. Apparatus for use in an analyzer and characterized in having no moving parts, for, in effect, alternately including a reference cell in a beam of radiation and removing the reference cell from the beam of radiation, the reference cell having a window for permitting the beam of radiation to enter the reference cell, said apparatus comprising in combination:

a layer of a material that has selectably a highly-reflective state and a highly-transmissive state, positioned in the beam of radiation ahead of the reference cell so that the beam of radiation is reflected from said layer when said layer is in its highly-reflective state and is transmitted by said layer when said layer is in its highly-transmissive state;

means for reflecting the radiation that has been transmitted into the reference cell back out through the window, so that when said layer is in its highly-transmissive state the beam of radiation is passed back through said layer;

means for alternating the state of said layer between the highly-reflective state and the highly-transmissive state;

means for collecting the total radiation reflected from said layer and emerging from said layer; and, means for comparing the total radiation collected when said layer is in the highly-reflective state with the total radiation collected when said layer is in the highly-transmissive state.

2. The apparatus of claim 1 wherein said layer is planar.

3. The apparatus of claim 1 wherein said layer is curved.

4. The apparatus of claim 1 wherein the reference cell has another window opposite said window and wherein said means for reflecting is outside of the reference cell and is located on the opposite side of the reference cell from said layer.

5. A method for use in an analyzer for, in effect, alternately including a reference cell in a beam of radiation and removing the reference cell from the beam of radiation, said reference cell having a window for permitting the beam of radiation to enter the reference cell, said method comprising the steps of:

positioning ahead of the reference cell a layer of a material that has selectably a highly-reflective state and a highly-transmissive state so that the beam of radiation is reflected from said layer when said layer is in its highly-reflective state and is transmitted into the reference cell when said layer is in its highly-transmissive state;

using a reflector to reflect back out through the window radiation that has been transmitted into the reference cell, so that when the layer is in its highly-transmissive state, the beam of radiation is passed back through the layer;

alternating the state of the layer between the highly-reflective state and the highly-transmissive state;

collecting the total radiation reflected from the layer and emerging from the layer and, comparing the total radiation collected when said layer is in the highly-reflective state with the total radiation collected when said layer is in the highly-transmissive state.

6. The method of claim 5 wherein the layer is planar.

7. The method of claim 5 wherein the layer is curved.

8. The method of claim 5 wherein the reflector is inside the reference cell.

9. The method of claim 5 wherein the reference cell has a second window opposite said window and wherein the reflector is outside of the reference cell and is located on the opposite side of the reference cell from the layer.

10. Apparatus for use in an analyzer and characterized in having no moving parts, for, in effect, alternately including a reference cell in a beam of radiation and removing the reference cell from the beam of radiation, the reference cell having a partially-reflective first window for permitting the beam of radiation to enter the reference cell, said apparatus comprising in combination:

a layer of a material that has selectably a highly-reflective state and a slightly-reflective state positioned to reflect the beam of radiation that has entered the reference cell back out through the first window;

means for alternating the state of said layer between the highly-reflective state and the slightly-reflective state;

means for collecting the total radiation reflected from the first window and emerging from the first window; and, means for comparing the total radiation collected when said layer is in the highly-reflective state with the total radiation collected when said layer is in the slightly-reflective state.

11. The apparatus of claim 10 wherein said layer is located inside the reference cell.

12. The apparatus of claim 10 wherein said layer is planar.

13. The apparatus of claim 10 wherein said layer is curved.

14. The apparatus of claim 10 wherein the reference cell has window to permit the beam of radiation to pass through the reference cell, and wherein said layer is located outside of the reference cell.

15. The apparatus of claim 14 wherein said layer is planar.

16. The apparatus of claim 14 wherein said layer is curved.

17. A method for use in an analyzer for, in effect, alternately including a reference cell in a beam of radiation and removing the reference cell from the beam of radiation, said reference cell having a partially-reflective first window for permitting the beam of radiation to enter the reference cell, said method comprising the steps of:

using a layer of a material that has selectably a highly-reflective state and a slightly-reflective state to reflect the beam of radiation that has entered the reference cell back out through the first window;

alternating the state of the layer between the highly-reflective state and the slightly-reflective state;

collecting the total radiation reflected from the first window and emerging from the first window; and, comparing the total radiation collected when the layer is in the highly-reflective state with the total radiation collected when the layer is in the slightly-reflective state.

18. The method of claim 17 wherein the layer is located inside the reference cell.

19. The method of claim 17 wherein the layer is planar.

20. The method of claim 17 wherein the layer is curved.

21. The method of claim 17 wherein the reference cell has a second window to permit the beam of radiation to pass through the reference cell and wherein the layer is located outside of the reference cell.

22. The method of claim 21 wherein the layer is planar.

23. The method of claim 21 wherein the layer is curved.

24. Apparatus for use in an analyzer and characterized in having no moving parts for alternately passing a beam of radiation through a reference cell and preventing the beam of radiation from passing through the reference cell, the reference cell having a first window for permitting the beam of radiation to enter the reference cell and a second window for permitting the beam of radiation to emerge from the reference cell, said apparatus comprising in combination:

a layer of a material that has selectably a highly-reflective state and a highly-transmissive state, positioned in the beam of radiation ahead of the reference cell so that the beam of radiation is reflected from said layer when said layer is in its highly-reflective state and is transmitted by said layer when said layer is in its highly-transmissive state to and through the reference cell;

means for alternating the state of said layer between the highly-reflective state and the highly-transmissive state;

means for collecting the radiation reflected from said layer when said layer is in its highly-reflective state;

means for collecting the radiation emerging from the second window of said reference cell when said layer is in its highly-transmissive state; and, means for comparing the collected radiation reflected from said layer when said layer is in its highly-reflective state with the collected radiation emerging from the second window of said reference cell when said layer is in its highly-transmissive state.

25. A method for use in an analyzer and characterized in having no moving parts, for causing a beam of radiation alternately to pass through a reference cell and to avoid passing through the reference cell, the reference cell having a first window to permit the beam of radiation to enter the reference cell and having a second window to permit the beam of radiation to emerge from the reference cell, said method comprising the steps of:

positioning in the beam of radiation ahead of the reference cell a layer of a material that has selectably a highly-reflective state and a highly-transmissive state, so that the beam of radiation is reflected from the layer when the layer is in its highly-reflective state and is transmitted by said layer when said layer is in its highly-transmissive state to and through the reference cell;

alternating the state of the layer between the highly-reflective state and the highly-transmissive state;

collecting the radiation reflected from the layer when the layer is in its highly-reflective state;

collecting the radiation emerging from the second window of the reference cell when the layer is in its highly-transmissive state; and, comparing the collected radiation reflected from the layer when the layer is in its highly-reflective state with the collected radiation emerging from the second window of the reference cell when the layer is in its highly-transmissive state.

26. Apparatus for use in an analyzer and characterized in having no moving parts, for determining the absorption that occurs when a beam of radiation passes through a reference cell having a first window that is partially reflective for permitting the beam of radiation to enter the reference cell and having a second window for permitting the beam of radiation to emerge from the reference cell, said apparatus comprising in combination:

a layer of a material that has selectably a transmissive state and an absorptive state and located to intercept the beam of radiation emerging from the second window of the reference cell so that the radiation intercepted by said layer is alternately substantially transmitted or substantially absorbed by said layer;

means for alternating the state of said layer between the transmissive state and the absorptive state;

means for collecting the radiation transmitted by said layer;

means for collecting the radiation reflected by the partially-reflective first window of said reference cell; and, means for comparing the collected radiation reflected by the partially-reflective first window with the collected radiation transmitted by said layer.

27. A method for use in an analyzer and characterized in having no moving parts, for determining the absorption that occurs when a beam of radiation passes through a reference cell having a first window that is partially-reflective for permitting the beam of radiation to enter the reference cell and having a second window for permitting the beam of radiation to emerge from the reference cell, said method comprising the steps of:

positioning adjacent the second window of the reference cell so as to intercept the beam of radiation emerging from the reference cell a layer of a material that has selectably a transmissive state and an absorptive state so that the beam of radiation intercepted by said layer is alternately substantially transmitted through the layer or substantially absorbed by said layer;

alternating the state of the layer between the transmissive state and the absorptive state;

collecting the radiation transmitted by the layer;

collecting the radiation reflected by the partially-reflective first window of the reference cell; and, comparing the collected radiation reflected by the partially-reflective first window with the collected radiation transmitted by the layer.

28. An article for use in a multi-component analyzer for selectively passing a preset fraction of a beam of polychromatic radiation through a selected one of N filters, where N is an integer, said article characterized by having no moving parts, said article comprising in combination:

N filters;

N independently-operably radiation gates each including a thin layer of a material that has selectably a transmissive state and a non-transmissive state depending on its temperature;

means connected to each thin layer for selectively and independently altering the state of each thin layer by altering its temperature;

a first opaque plate having N apertures, each aperture coverd by one of said N filters; and, a second opaque plate positioned parallel to but spaced from said first opaque plate and having N apertures each of which overlies, in whole or in part, only one of the apertures of said first opaque plate when said first and second opaque plates are so positioned, each of the apertures of said second opaque plate covered by one of said N independently-operable radiation gates.

29. An article for use in a multi-component analyzer for seelctively reflecting a preset fraction of a beam of polychromatic radiation through a selected one of N filters, where N is an integer, said article characterized by having no moving parts, said article comprising in combination:

N filters;

N independently-operable selective reflectors each including a third layer of a material that has selectably a highly-reflective state and a slightly-reflective state depending on its temperature;

means connected to each thin layer for selectively and independently altering the state of each thin layer by altering its temperature;

a first opaque plate located to intercept the entire beam of polychromatic radiation and having N apertures, each aperture covered by one of said N filters; and, a second plate positioned parallel to but spaced from said first opaque plate, said N independently-operable selective reflectors mounted on said second plate directly behind the apertures in said first opaque plate, so that all of the radiation passing through one of the apertures falls on the corresponding selective reflector and no other.

30. A multi-component analyzer characterized by having no moving parts, and having means for producing a beam of polychromatic radiation and for passing the beam through a sample to be analyzed to produce a characterized beam, comprising in combination:

first means having no moving parts, and including more than one filter, and located to intercept the characterized beam, for selectively passing a preset fraction of the characterized beam through a selected one of the more than one filter to produce a filtered beam in response to an applied first electrical signal;

a detector for producing an electrical output signal related to the intensity of the radiation applied to it;

second means having no moving parts and including a reference cell, and located to intercept the filtered beam, responsive to an applied second electrical signal for alternately either applying the filtered beam directly to said detector or first passing the filtered beam through the reference cell and then applying the beam that has passed through the reference cell to said detector;

third means connected to said first means and to said second means for generating the first electrical signal and the second electrical signal and for applying the first electrical signal and the second electrical signal to said first means and to said second means, respectively; and, means connected to said detector for comparing the electrical output signal produced by said detector when the filtered beam is passing through the reference cell with the electrical output signal produced by said detector when the filtered beam is applied directly to said detector.

31. A method for use in a multi-component analyzer characterized in having no moving parts, and having means for producing a beam of polychromatic radiation and for passing the beam through a sample to be analyzed to produce a characterized beam, said method comprising the steps of:

locating a filter selector that has no moving parts so as to intercept the characterized beam;

applying a first electrical signal to the filter selector to select for use one of more than one filters, so that a filtered beam is produced;

locating a reference cell inserter that has no moving parts so as to intercept the filtered beam;

applying a second electrical signal to the reference cell inserter alternately to insert into and to remove from the filtered beam a reference cell, so that an output beam is produced; and, positioning a detector so as to intercept the output beam.

32. A multi-component analyzer characterized by having no moving parts, and having means for producing a beam of polychromatic radiation and for passing the beam through a sample to be analyzed to produce a characterized beam, comprising in combination:

first means having no moving parts and including a reference cell, located to intercept the characterized beam, and responsive to an applied first electrical signal for producing an output beam that consists alternately of either the characterized beam or the beam obtained by passing the characterized beam through the reference cell;

a detector for producing an electrical output signal related to the intensity of the radiation applied to it;

second means having no moving parts and including more than one filter, and located to intercept the output beam of said first means, for selectively passing a preset fraction of the output beam through a selected one of the more than one filter to produce a filtered beam in response to an applied second electrical signal, and for applying the filtered beam to said detector;

third means connected to said first means and to said second means for generating the first electrical signal and the second electrical signal and for applying the first electrical signal and the second electrical signal to said first means and to said second means, respectively; and, means connected to said detector for comparing the electrical output signal produced by said detector when the characterized beam is passing through the reference cell with the electrical output signal produced by said detector when the characterized beam is passed directly to said second means.

33. A method for use in a multi-component analyzer characterized in having no moving parts, and having means for producing a beam of polychromatic radiation and for passing the beam through a sample to be analyzed to produce a characterized beam, said method comprising the steps of:

locating a reference cell inserter that has no moving parts so as to intercept the characterized beam;

applying a first electrical signal to the reference cell inserter alternately to insert into and to remove from the filtered beam a reference cell, so that an output beam is produced;

locating a filter selector that has no moving parts so as to intercept the output beam;

applying a second electrical signal to the filter selector to select at least one of more than one filters, so that a filterd beam is produced; and, positioning a detector so as to intercept the filtered beam.

34. An analyzer characterized by having no moving parts, and having means for producing a beam of radiation and for passing the beam through a sample to be analyzed to produce a characterized beam, comprising in combination:

a detector for producing an electrical output signal related to the intensity of the radiation applied to it;

first means having no moving parts and including a reference cell, located to intercept the characterized beam, and responsive to an applied electrical signal for producing an output beam that consists alternately of the characterized beam and of the beam obtained by passing the characterized beam through the reference cell, said first means applying the output beam to said detector;

second means electrically connected to said first means for generating the electrical signal and for applying the electrical signal to said first means; and, third means connected to said detector for comparing the electrical output signal produced by said detector when the output beam consists of the characterized beam with the electrical output signal produced by said detector when the output beam consists of the beam obtained by passing the characterized beam through the reference cell.

35. A method for use in an analyzer characterized in having no moving parts, and having means for producing a beam of radiation and for passing the beam through a sample to be analyzed to produce a characterized beam, said method comprising the steps of:

locating a reference cell inserter that has no moving parts so as to intercept the characterized beam;

applying an electrical signal to the reference cell inserter alternately effectively to insert into and to remove from the characterized beam a reference cell, so that an output beam is produced that alternately has and has not passed through the reference cell; and, positioning a detector so as to intercept the output beam.

* * * * *